(12) United States Patent
Petrali et al.

(10) Patent No.: US 6,555,334 B2
(45) Date of Patent: Apr. 29, 2003

(54) FREE FLOATING CRYOSTAT SECTIONS FOR USE IN LIGHT AND ELECTRON MICROSCOPY AND METHOD

(75) Inventors: John P. Petrali, Churchville, MD (US); Robert Kwai Kan, Abingdon, MD (US); Tracey A. Hamilton, Bel Air, MD (US); Susan B. Oglesby-Megee, Rising Sun, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/949,572

(22) Filed: Sep. 10, 2001

(65) Prior Publication Data

US 2003/0049719 A1 Mar. 13, 2003

(51) Int. Cl.[7] ................................................ G01N 1/30
(52) U.S. Cl. ................................... 435/40.5; 435/40.52
(58) Field of Search ............................. 435/40.5, 40.52

(56) References Cited

U.S. PATENT DOCUMENTS 4,971,783 A    11/1990  Bolton et al. ................. 424/3
6,252,130 B1 *  6/2001  Federoff ...................... 800/14

OTHER PUBLICATIONS

Harmon (1987). A technique for preparation of brain tissue for combined LM and EM analysis. The Journal of Histochemistry 10 (1): pp 35–36.*

Anthony et al. (1986). Combined light and electron microscope immunocytochemical localization of scattered peptidergic neurons in the central nervous system. The American Journal of Anatomy 175: pp179–195.*

* cited by examiner

*Primary Examiner*—Ralph Gitomer
(74) *Attorney, Agent, or Firm*—Elizabeth Arwine (57) ABSTRACT

A method is described of viewing a single tissue sample with a light microscope and an electron microscope. A tissue sample is cryopreserved, cryo sectioned and then floated in a cryoprotectant solution on a surface of a glass slide or in a well and is viewed by light microscopy. The step of floating the tissue sample does not destroy said tissue sample for subsequent electron microscope viewing. The same tissue sample is then prepared by conventional ultrastructural processing for viewing by electron microscopy. The data from the light microscope and electron microscope images of selected sites of the same tissue sample can be compared and analyzed.

13 Claims, 10 Drawing Sheets

FREE FLOATING CRYOSTAT SECTIONS FOR USE IN LIGHT AND ELECTRON MICROSCOPY AND METHOD

FIELD OF INVENTION

This invention relates to the field of histology and immuno-histology using immunoelectron microscopy. More specifically, this invention relates to the field of free-floating cryostat sections for use in light and electron microscopy to bridge the gap between these two viewing mediums.

BACKGROUND OF THE INVENTION

In many instances, a scientist studying a histological sample desires to view a tissue specimen with both a light microscope and also with an electron microscope to obtain information that is unique to each discipline. Unfortunately, there is no known way to view the exact same tissue sample with both devices. No medium has been developed that allows the scientist to move a single tissue specimen from one device to the other.

In the past, two separate tissue samples from the same subject were required for viewing with the separate devices. A comparison had to be made to bridge the gap between the results of the light microscope and the electron microscope. However, the comparison of two separate samples has inherent limitations.

Processing of tissues for electron microscopy routinely required that tissues be chemically fixed. Some of the practices that have been used are thick paraffin embedded tissue sectioning, and microwave processing. These techniques require chemical fixation with formaldehyde or combinations of aldehydes. In regard to paraffin processing, thick sections subsequently processed for electron microscopy are structurally compromised as a result of the necessary exposure to highly volatile reagents required for adequate paraffin processing (zylenes, toluenes). In the case of microwave energy, the tissues are typically subjected to a dilute concentration of chemical fixatives for a short time (seconds) prior to exposing the tissue to microwave processing. The effect of the microwave is to accelerate the chemical fixation process by superheating and/or by producing rapidly oscillating water molecules within the tissue. Both effects of heat and water oscillations act to etch or open the tissue to the dilute fixative.

However, in studies that address the preservation of labile structural proteins, chemical fixation is contraindicated. Therefore other means of preservation were pursued. Procedures presently used that circumvent chemical fixation are cryofixation, microwave-assisted fixation and vibratoming.

Cryofixed tissues for electron microscopy require that the tissues then be cryosectioned through the use of cryoultramicrotomes. These procedures (cryofixation and cryoultramicrotomy) are terribly expensive (cryoultratomes) and extremely labor intensive requiring committed technical dedication by a well-trained technical staff. Moreover, light microscopic examinations and electron microscopy examinations within the same study require the use of separate and distinct tissue sections for each discipline.

Microwave assisted fixation uses chemical fixation that is accelerated by action of the microwave.

Vibratomed fresh (unfixed tissues) for subsequent processing is yet another method that has been employed. "Vibratoming" makes use of a rapidly oscillating microtome blade which sections through unfixed tissue. However only certain tissues can be vibratomed. The types of unfixed tissues that can be vibratomed successfully are terribly restricted with skin being the least desirable.

In these currently existing practices, there are the following limitations: 1. All except vibratoming require some form of chemical fixation to retain the structural integrity of the tissue sample especially at the ultrastructural level (electron microscopy); 2. All practices that require chemical fixation preclude the preservation of some important antigenic determinants of skin basement membrane proteins; 3. Loss of antigenic determinants then precludes the use of special staining practices (immunochemistry) which would visualize these proteins at light and electron microscopy levels.

As stated, there are particular types of tissues that are especially difficult to work with for purposes of microscope viewing. One such tissue type is skin basement membrane zone. Since skin basement membrane protein components are labile to conventional chemical fixation and since skin is not amenable to vibratome sectioning, frozen skin sections are routinely used for light microscopic immunohistochemical study of the skin basement membrane zone. This requires the use of conventional frozen sections. However, inherent limitations of conventional frozen sections, including compromised morphology and requirement for glass slide-mounting, usually limit study solely to the light microscopic level. These same sections cannot subsequently be used for observation by an electron microscope.

Sections of skin basement membrane zone that are mounted on slides for use with light microscopes are routinely discarded after they are viewed under the light microscope. New and separate sections from the same animal specimen must be taken for preparation and viewing by an electron microscope. This process is both expensive, time consuming and requires comparison of two separate and distinct tissue specimens. A single specimen cannot be subsequently used for viewing with the electron microscope.

Immunoelectron microscopy remains a method of choice for determining the precise immunoanatomical location of antigens at the ultrastructural level (Schaumburg-Lever, 1995; 1999). This technique has been used extensively for mapping the distribution of epidermal-dermal junction proteins in various inherited bullous diseases including bullous pemphigoid (Bedane et al., 1997) and dystrophic epidermolysis bullosa (Bruckner-Tuderman et al., 1989). Recently, immunoelectron microscopy was employed to study basement membrane proteins in sulfur mustard-induced cutaneous vesicating lesions (Monteiro-Riviere and Inman, 1995; Petrali and Oglesby-Megee, 1997). A persistent concern of immunoelectron microscopy is the preservation of ultrastructural morphology while simultaneously maintaining the immunoreactivity of proteins of interest. This concern becomes a special problem when antigenic epitopes of proteins are vulnerable to damage by chemical fixation rendering antigenic binding sites insensitive to antibody labeling.

The present invention advances the use of immunoelectron microscopy to study the immunopathology of the skin basement zone induced by the chemical vesicating agent sulfur mustard. Since proteins of the skin basement membrane zone are susceptible to chemical fixation-induced damage, immunoidentification of basement membrane proteins is restricted largely to unfixed cryostat sections mounted onto microscope slides. Further evaluation of these sections by electron microscopy requires that tissue be separated from slides by the "pop-off" method introduced by Bretschneider and colleagues (1981). This useful, but arduous technique causes loss of valuable material when tissue sections do not separate from the slide cleanly and often yields poor ultrastructural detail (Bretschneider et al., 1981). To circumvent these technical problems, the present invention employs a procedure using unfixed, free-floating frozen skin sections for immuno-detection of cutaneous basement membrane zone components of interest in the study of vesicating skin lesions. The adaptation of a free-floating method to bridge the light microscope and electron microscope gap in the area of basement membrane biology is novel and can be readily applied to all areas of basement membrane research.

The present invention is especially advantageous because it avoids chemical fixation by using cryofixation which promotes the stability of labile proteins, performs procedures to identify antigenicity (viability) of proteins and their anatomical locations (immunohistochemistry), performs these procedures on the same tissue section, processes the same immunostained tissue section for both light and electron microscopic analysis, and performs these procedures on skin tissue that is not amenable to vibratome sectioning.

In addition to the above, the application of free floating sections allows for the use of other cytochemical procedures beyond that of immunohistochemistry. For example the tissue section can be subjected to cytochemical study (study of specific chemical reactions to the exclusion of others), penetration/absorptive studies of topically applied reagents, extraction studies (removing structural/chemical entities), enzyme analysis and enzyme traffic pathways, reduces problems of antibody penetrations by permitting the apposition of antibodies to all free floating section surfaces. The free-floating parameter of the invention also removes problems associated with serial sectioning. By way of explanation, serial sectioning is a required tissue sectioning practice of generating tissue sections that closely follow each other at a given spatial cadence. The purpose is to achieve an appreciation of spatial relationships of specific anatomical/subcellular entities within a given expanse of tissue. With the present invention, a given anatomical relationship is achieved with one section for both light and electron microscopic analysis.

The present invention, as stated above, is useful for studying the pathogenesis of vesicants (blistering agents) on skin. Since the skin basement membrane zone is the target of vesicants, the present invention permits a research tool that preserves this zone and does not compromise zone function (protein viability). Since additional studies would eventually incorporate accelerated diagnosis through the use of skin biopsies, we have established a process that accommodates histopathology (light microscopic pathology) and ultrastructural pathology (electron microscopy) in one analytical substrate/system, namely free-floating cryostat skin sections.

OBJECTS OF THE INVENTION

An object of the invention is to provide a type of specimen for viewing that can bridge the gap between light and electron microscope use.

Another object of the invention is to provide a method that provides ease of progressive processing of the same tissue specimen from light microscopy to electron microscopy.

Another object of the invention is to provide a method of preparation of a tissue specimen that can be viewed by both light and electron microscopes.

Another object of the invention is to provide a free-floating cryostat section that can be processed as routine tissue specimens and can be subjected to a variety of special staining procedures including immunohistochemistry.

Another object of the invention is to provide a method that is useful when results of immunolabeling experiments need to be elucidated quickly at histological and ultrastructural levels as required for diagnostic and accelerated investigative strategies.

SUMMARY OF THE INVENTION

The invention relates to a method of viewing a single tissue sample with a light microscope and an electron microscope. First, a desired tissue sample is selected, cryopreserved and cryosectioned to an appropriate thickness, usually around 50–70 microns, and preferably 60 microns thick. This thickness resists problems associated with sequential processing. For information purposes, the typical cryostat section thickness for use with glass-mounted sections is 6–10 microns. The sectioned tissue sample is then floated in a solution on a surface of a glass slide or in a well. The floating of said tissue sample permits viewing by a light microscope. In addition, the tissue sample may be stained and subjected to various immunohistochemical procedures before viewing with the light microscope.

The step of floating the tissue sample does not destroy the tissue sample for electron microscope viewing. The same tissue sample is then prepared for electron microscopy. This usually involves removing the undamaged floated tissue sample from the glass slide or well and embedding it in resin. The embedding of the tissue sample in resin can be accomplished by methods known in the art for embedding tissue samples and viewing them by electron microscopes. The tissue sample is then viewed by an electron microscope. The data from the light microscope and electron microscope images of the same tissue sample can be compared and analyzed.

DETAILED DESCRIPTION

In the present study, unfixed, free-floating cryostat sections that can be processed as routine tissue specimens and can be subjected to a variety of special staining procedures including immunohistochemistry are used. Especially useful is the ease of progressive processing of the same tissue specimen from light microscopy to electron microscopy. In this regard, the method renders itself useful when results of immunolabeling experiments need to be elucidated quickly at histological and ultrastructural levels, as required in diagnostic and accelerated investigative strategies.

Skin basement membrane zone proteins selected for use were α6 integrin, pan-laminin, collagen type IV, and collagen type VII. Alpha 6 integrin is a hemidesmosomal-associated transmembrane protein that anchors basal cells to the underlying dermis via interaction with anchoring filaments. Laminin is a major glycoprotein component of anchoring filaments that function as an adhesion ligand to integrins. Collagen type IV is a component of the lamina densa of the skin basement membrane and anchoring plaques in the papillary dermis. Collagen type VII is a major component of anchoring fibrils that connect the lamina densa to the papillary dermis through direct connection to the anchoring plaques. Complex interactions of these proteins at the level of the basement membrane maintain the attachment between the epidermis and the dermis. Therefore, alterations in the conformation of these proteins can seriously compromise the structural integrity of the basement membrane zone, making the epidermal-dermal interface more susceptible to separation during vesication. This is also known as blistering. The invention addresses the usefulness of unfixed, free-floating cryostat sections of human skin for the immunodetection of selected basement membrane zone proteins at the light and electron microscopic levels.

a. Section Preparation:

The important feature of this free-floating procedure is the use of 30% sucrose cryoprotectant solution as a floating media immediately following cryosectioning. This cryoprotectant solution was used to prevent cryostat sections from fragmenting during thawing. When frozen sections were floated in phosphate buffered saline instead of cryoprotectant solution, the skin fragmented, destroying all morphology.

b. Immunostaining:

"Immunostaining" refers to the final staining profiles of the immunohistochemically stained tissues. By light microscopy, those proteins which are immunohistochemically identified are stained dark brown (diaminobenzidine). The unreactive tissue is not stained. By electron microscopy, the specific reactive sites are electron dense (black).

c. Immunoelectron Microscopy:

All procedures for immunoelectron microscopy, including embedding in resin, mounting sections on grids and counterstaining are standardized procedures.

Human breast skin obtained from cosmetic correction surgery (National Disease Recovery Interchange, Philadelphia, Pa.) was cut into strips approximately 8 mm long by 5 mm wide with razor blades with a single straight cut through the full thickness of the skin. Sawing motions were avoided to minimize undesired mechanical skin separation at the epidermal-dermal junction. Skin strips were then trimmed to remove excess dermis so that only a small portion of the upper dermis remained. For freezing, skin strips were wrapped in gauze, plunge-frozen in chloro difluoromethane refrigerant (Freon 22), placed in aluminum foil pouches and stored at 70° C.

While tissues were prepared for cryosectioning, a Teflon-coated, 12 well plate filled with a cryoprotectant solution (500 ml deionized water, 300 g sucrose, 300 ml ethylene glycol, 1.59 g sodium phosphate monobasic, 5.47 g sodium phosphate dibasic, 9.0 g sodium chloride, 10 g polyvinylpyrrolidone, final volume adjusted to 1 liter with deionized water) was chilled in a cryostat set at −24° C. Although this cryoprotectant solution was originally formulated for long-term storage of brain sections (Watson et al., 1986), in this protocol the cryoprotectant solution was used to minimize fragmentation of skin sections during thawing. Frozen skin sections, cut at 60μ, were then picked up with a paintbrush and individually floated in cryoprotectant. Extreme caution was taken to make sure sections were floated in the center of wells to prevent them from sticking to sides of the wells. When sections were equilibrated with cryoprotectant solution as evidenced by their transparent appearance, they were then removed from the cryostat chamber and thoroughly rinsed three times, 15 min. each, with cold phosphate buffered saline (PBS, 4° C.) to remove excess cryoprotectant solution.

All immunohistochemical procedures were performed at 4° C. to minimize tissue autolysis. Indirect immunohistochemical localization of rabbit anti-human α6 integrin (1:100; Chemicon International Inc.), mouse anti-human collagen type VII (1:100 Sigma), rabbit anti human collagen IV (1:100; Chemicon International Inc. ) was performed using the avidin-biotin-peroxidase complex (ABC) method described by Hsu et al. (1981), J Histo Cyto. 29(4: 577–580, incorporated herein by reference. Care was taken to avoid touching the skin sections with disposable pipets when adding or removing immunochemical reagents.

The antibodies that were used in the present invention are chain specific. These antibodies are useful in their immunospecificity. They have been used for many years clinically to characterize immunobullous diseases and to determine extent, penetration and boundaries of skin tumors.

Following three rinses with PBS, 10 minutes each, to remove cryoprotectant solution, skin sections were incubated in 5% normal serum for 30 minutes to suppress endogenous tissue immunoglobulin that could react with the biotinylated secondary antibody. Skin sections were then sequentially incubated in primary antibody for 18 hours, biotinylated secondary antibody diluted 1:200 for one hour (Vector Laboratories), and ABC solution for 30 minutes (Vector Laboratories). Finally, immunoreaction product was visualized with a mixture of diaminobenzidine tetrahydrochloride (DAB) and urea hydrogen peroxide (Sigma). After appropriate levels of specific staining intensity were attained by the immunostaining technique, sections were washed in deionized water and kept at 4° C. overnight in Karnovsky's fixative consisting of 2.5% glutaraldehyde and 1.6% paraformaldehyde in 0.1M sodium caccodylate. Skin sections processed without primary antibody were used as method controls.

The following day, immunostained sections were washed thoroughly in three changes of 0.1M sodium cacodylate buffer (21.40 g sodium cacodylate, 900 ml deionized water, final volume adjusted to 1 liter with deionized water, adjusted pH to 7.4 with 1.0N HCl) to remove fixative, transferred to a petri dish and examined under a dissecting microscope to locate specific areas of interest. The selected areas were excised from the sections with a scalpel and temporarily wet-mounted on glass slides for light microscope examination and photomicroscopy.

After free floating sections were photographed for light microscopy, they were post fixed in 1% osmium tetroxide in 0.1M sodium cacodylate buffer for 5 minutes, followed by three rinses in 0.1 M sodium cacodylate buffer.

For post fixation the sections were transferred with a paint brush tip to a vial containing the osmium tetroxide. Sections were then dehydrated in increasing concentrations of ethanol, cleared in propylene oxide and embedded in epoxy resin (Polybed 812) by methods standard in the art. Ultra thin sections prepared with a diamond knife were collected on copper or nickel mesh grids, counterstained with lead citrate and uranyl acetate and analyzed by transmission election microscopy (JEOL 1200 EX) by methods standard in the art.

Figure 1A:
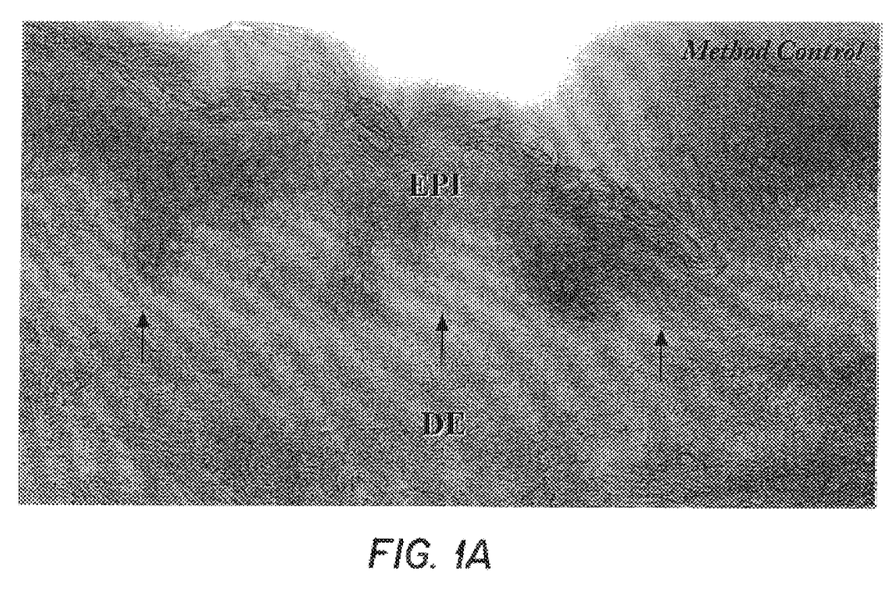
FIG. 1A is a sectional view of a wet-mounted cryostat section of a method control viewed by a light microscope according to the invention.
Figure 1B:
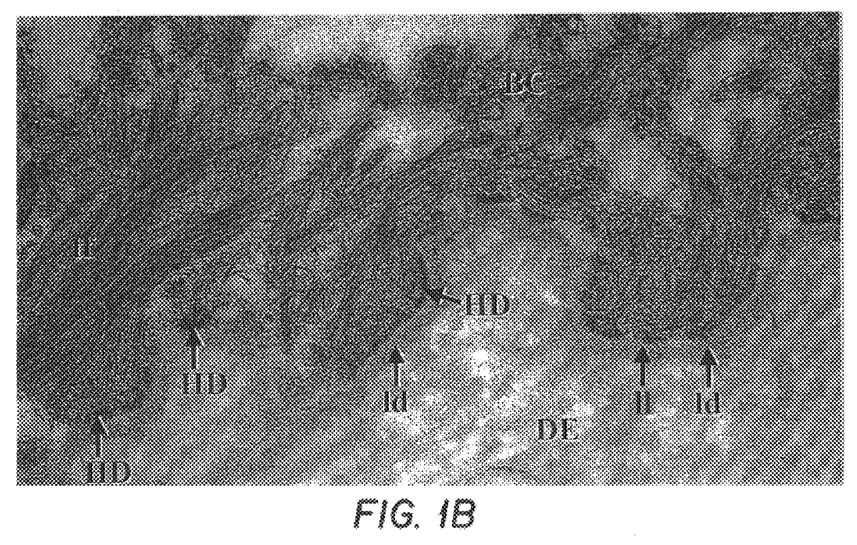
FIG. 1B is a sectional view of the same cryostat section viewed by an electron microscope according to the invention.

Results:

The results indicated that the free-floating method of the present invention permits the examination of the same frozen skin sections for both light microscopy and electron microscopy. Free-floating skin sections immunostained by the ABC immunohisochemistry without primary antibody showed no specific immunoreactivity to the epidermal dermal junction; magnification 66× (FIG. 1A). At the electron microscopic level, the ultrastructural integrity of the basement membrane zone was clearly maintained; magnification 60 k (FIG. 1B).

In all the figures, EPI is epidermis, DE is dermis, BC is basal cell; tf is tonofilaments, HD is hemidesmosome, ll is lamina lucida, and ld is lamina densa.

Figure 2A:
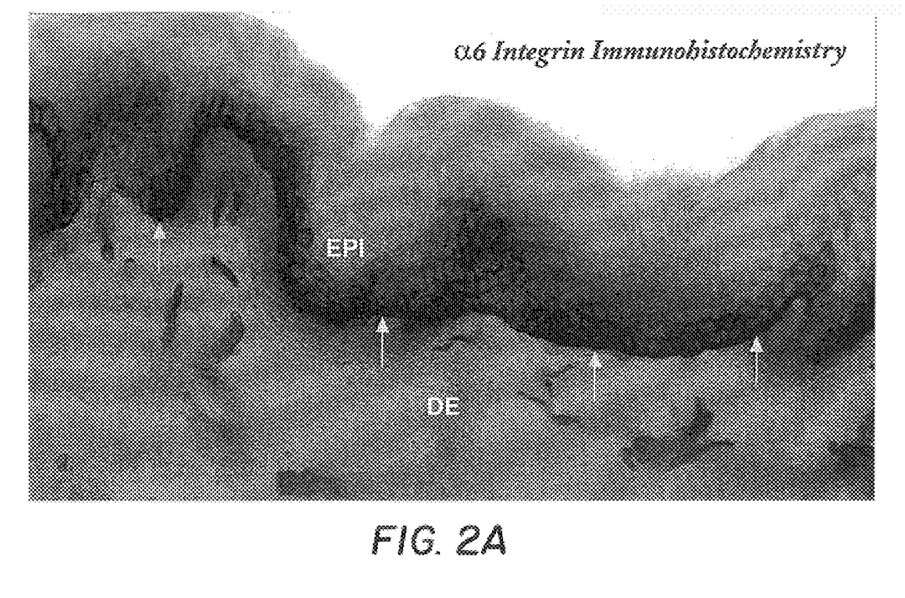
FIG. 2A is a sectional view of a wet-mounted cryostat section of a light microscopic examination of immunohistochemical staining for α6 integrin showing continuous immunoreactivity to basement membrane zone.
Figure 2B:
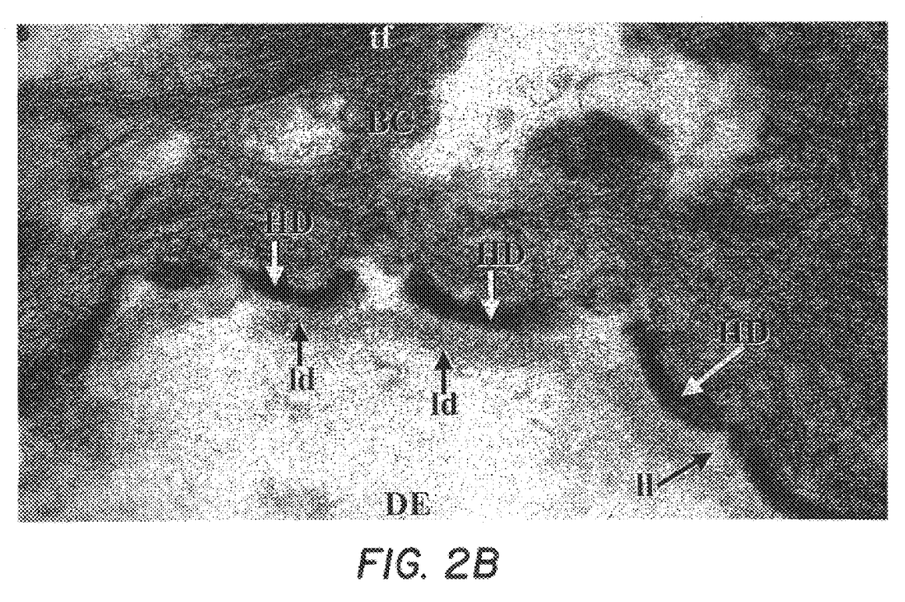
FIG. 2B is a sectional view of an electron microscopic examination of the section of FIG. 2A demonstrating precise anatomical immunolocalizations of α6 integrin to hemidesmosomal plaques of epidermal basal cells.
Figure 3A:
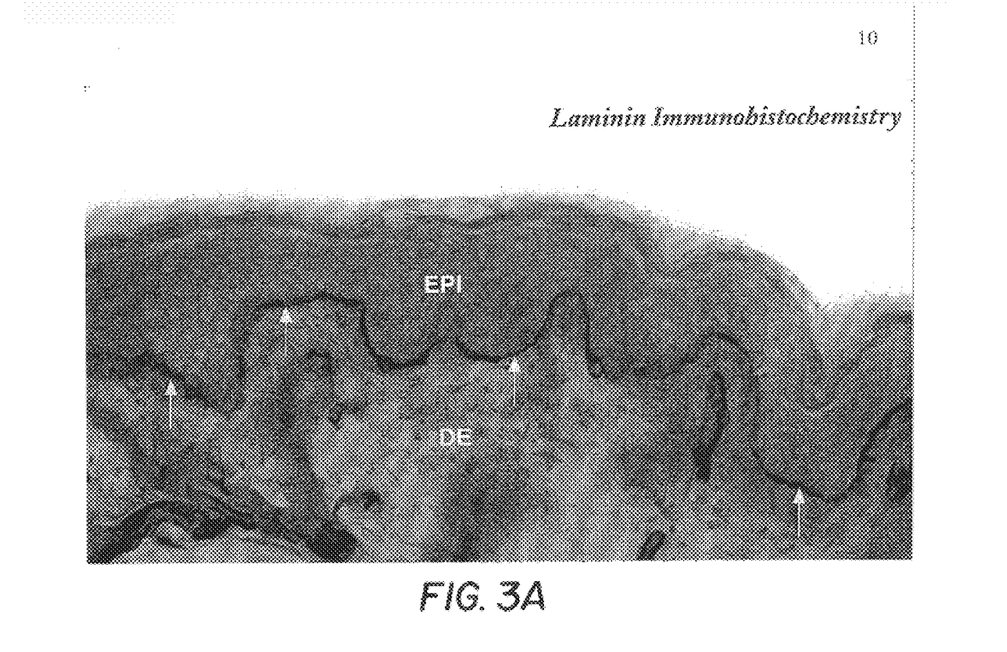
FIG. 3A is a sectional view of light microscopic examination of immunohistochemical staining for laminin showing continuous immunoreactivity to basement zone.
Figure 3B:
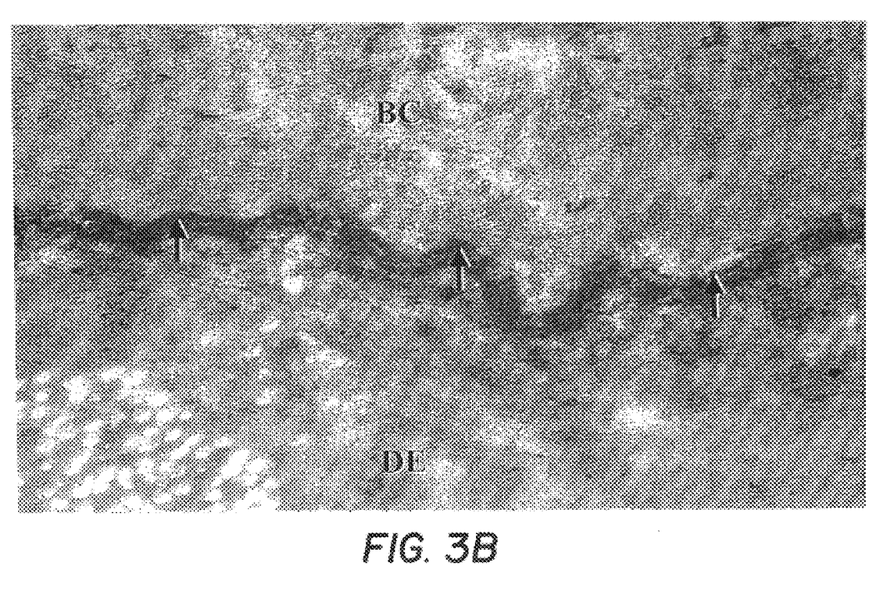
FIG. 3B is a sectional view electron microscopic examination of the section of FIG. 3A showing the precise anartomical immunolocalizations of laminin to lamina lucida.
Figure 4A:
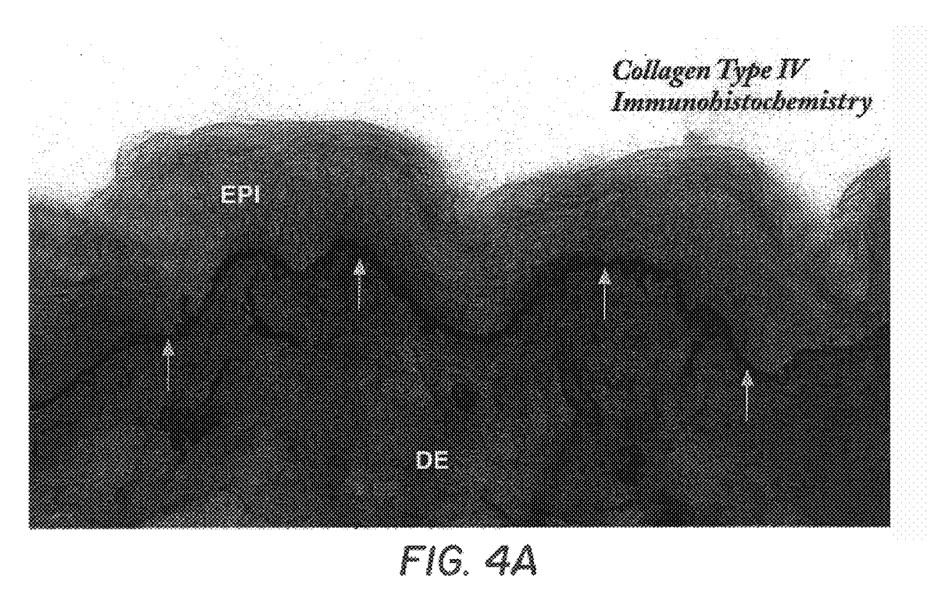
FIG. 4A is a sectional view of a light microscopic examination of immunohistochemical staining for collagen type IV showing continuous immunoreactivity to basement membrane zone.
Figure 4B:
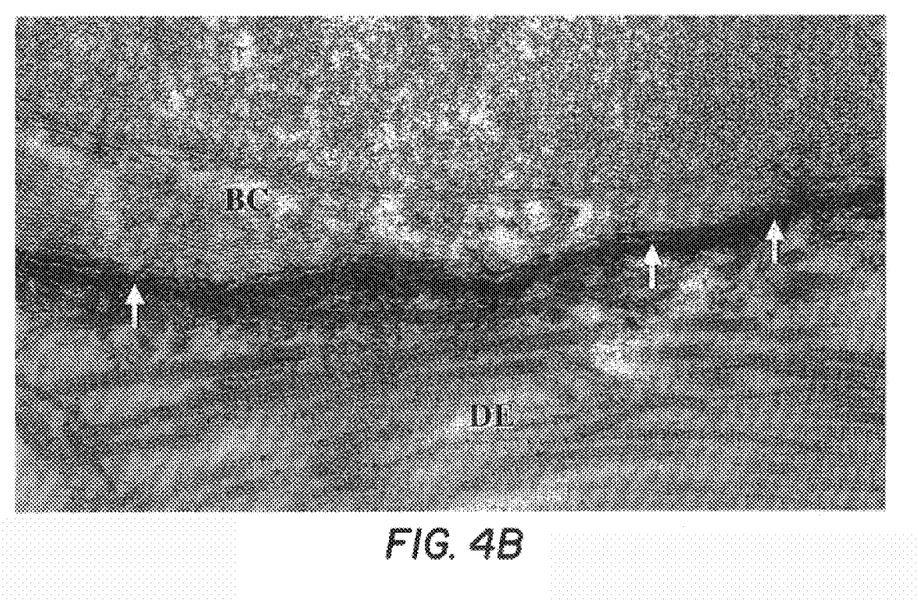
FIG. 4B is a sectional view of an electron microscopic examination of section of FIG. 4A showing precise anatomical immunolocalization of collagen type IV to lamina densa.
Figure 5A:
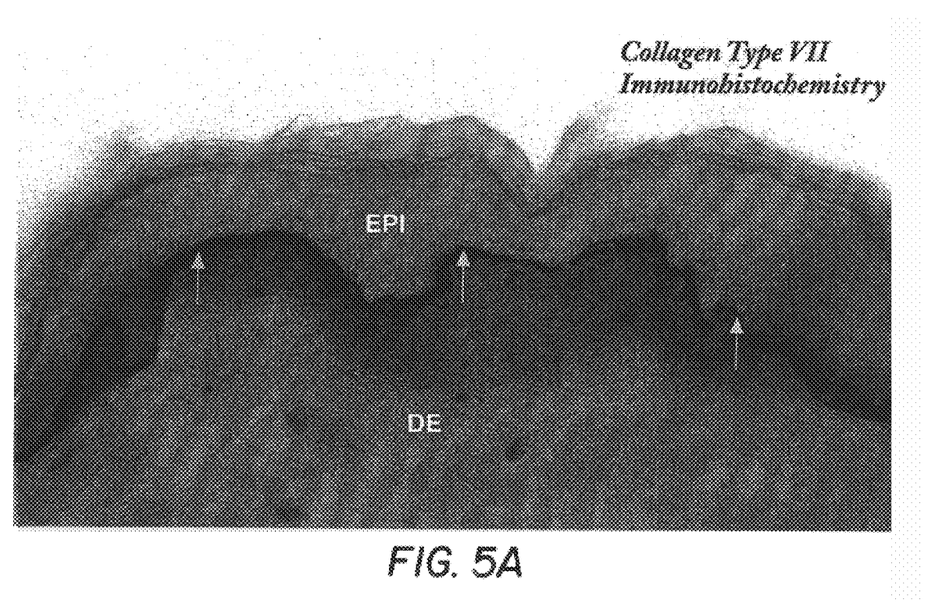
FIG. 5A is a sectional view of a light microscopic examination of immunohistochemicalstaining for collagen type VII showing continuous immunoreactivity to basement membrane zone.
Figure 5B:
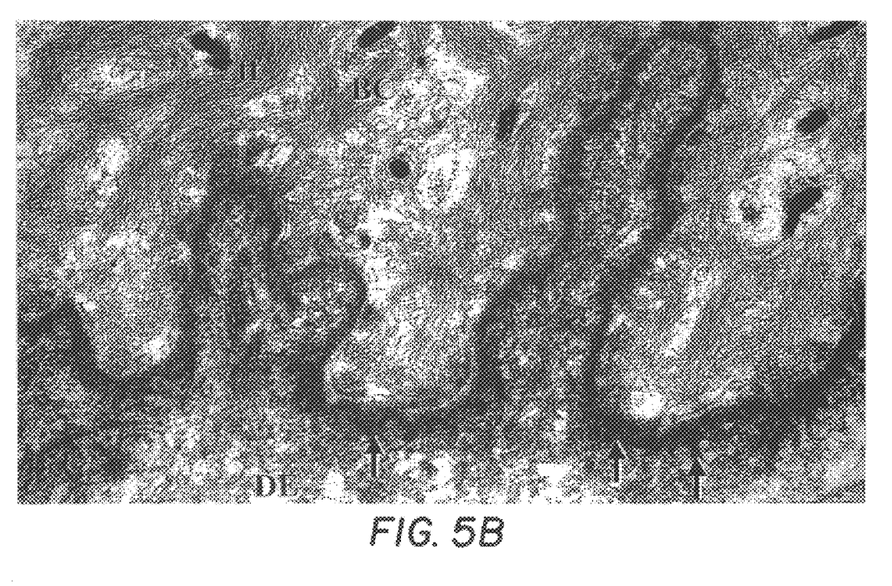
FIG. 5B is a sectional view of an electron microscopic examination of the section of FIG. 5A showing precise anatomical immunolocalization of collagen type VII to lower lamina densa and anchoring fibrils.

At the light microscopic level, free-floating skin sections immunolabeled using antiserum against human α6 integrin, laminin, type IV collagen or type VII collagen showed specific immunoreactivity along the epidermal-dermal junction. Alpha 6 integrin immunoreactivity was specifically localized to the outer hemidesmosamal plaques of epidermal basal cells. FIG. 2A, light microscopic examination of immunohistochemical staining for α6 integrin showing continuous immunoreactivity to basement membrane zone (arrows) at a magnification of 66×. FIG. 2B shows electron microscopic examination of the same section demonstrating precise anatomical immunolocalizations of α6 integrin to hemidesmosomal plaques of epidermal basal cells (arrows) at a magnification of 75 k. Immunoreactivity of laminin was localized to the lamina lucida of the basement membrane zone with same immunoreactivity in the upper portion of the lamina densa (FIG. 3). FIG. 3A shows laminin immunolabeling by light microscopy at a magnification of 66× and FIG. 3A shows laminin immunolabeling by electron microscopy at a magnification of 60 k. Collagen type VII immunoreactivity was specific to the lower aspect of the lamina densa and to the sublamina densa (FIG. 4). FIG. 4A shows collagen Type IV immunolabeling by light microscopy at 66× and FIG. 4B shows collagen Type IV immunolabeling by electron microscopy at 60 k. In the sublamina densa, collagen type VII immunoreaction products appeared as tubular projections originating from the lamina densa extending to the papillary dermis (FIG. 5). FIG. 5A shows collagen type VII immunolabeling by light microscopy at 66× and FIG. 5B shows collagen type VII immunolabeling by electron microscopy at 45 k.

The results of the present invention demonstrate the value of free-floating cryostat sections for rapid microscopic examination of skin basement membrane proteins at both the light and electron microscopic levels and demonstrates its potential for use in diagnostic strategies of sulfur mustard toxicity.

At the light microscopic level, human skin samples showed immunoreactivity of all the selected proteins to the basement membrane zone. At the electron microscopic level, the same sections exhibited acceptable ultrastructure and precise high resolution anatomical immunolocalization of the proteins. Alpha6 integrin was specifically immunolocalized to the hemidesmosomal plaques of the basal cells; laminin was immunodistributed at the lower lamina lucida and at the upper level densa; collagen type IV was immunolocalized to the entire lamina densa; and collagen type IV was immunolocalized to the entire lamina densa; and collagen type VII was immunoreactive to the lower lamina densa and anchoring fibrils of the sublamina densa.

These observations are in strong agreement with the other basement membrane protein localization studies which use complex microwave methodology (Petrali and Mills, 1999, Microwave-assisted immunoelectron microscopy of skin: localization of laminin, type IV collagen, and bullous pemphigoid antigen. J. Toxicol. Cutan Ocular Toxicol 18(4) :341–348.), expensive cryoultramicrotomy practices (Masunaga et al, 1996, Localization of laminin-5 in the epidermal basement membrane, J Histochem Cytochem 44(11): 1223–1230.), cryofixation and cryosubstitution technology (Shimizu et al., 1990, Epidermolysis bullosa acquisita antigen and the carboxy terminus of type VII collagen have a common immunolocalization to anchoring fibrils and lamina densa of basement membrane, Br J Dermatol 122(5): 577–585). The free-floating method addressed in this invention disclosure does not alter ultrastructural morphology and preserves the antigenicity of selected basement membrane zone proteins at relatively low cost and low technical severity.

The present invention provides evidence that the use of free-floating, cryostat sections is a valuable method for ultrastructural immunoidentification of cutaneous basement membrane zone proteins without the usual requirement of expensive cryoprocessing or microwave superheating. This simple procedure can be performed in a laboratory with basic electron microscopy facilities. Using the technique of the present invention, both antigenic and morphological structures of the basement membrane zone were preserved, precise immunolocalizations of all selected proteins are presented, tissue processing from light to electron microcopy of the same tissue sections was accelerated, and correlated. In addition, the difficulties with management of tissue spatial arrangements usually experienced with tissue serial sectioning are eliminated. These desirable applications are especially important when results of immunostaining need to be established quickly at the level of light and electron microscopy, and will be beneficial in the rapid diagnosis and characterization of target antigens associated with vesicating skin lesions.

Other tissue organs not suitable for vibratome sectioning can also be processed by the method of the present invention.

EXAMPLES

Example 1

Fresh skin samples frozen in the chlorodifluoromethoane refrigerant Freon 22 were sectioned at 60μ and individually placed in wells filled with cryoprotectant solution as formulated by deOlmos and colleagues. DeOlmos, J. S., H. Hardy and L. Heimer: (1978) J. Comp. Neurol. 181: 213–244. Immunohistochemistry was performed using the avidin-biotin-peroxidase complex (ABC) method described by Hsu and coworkers. Hsu, S-M, L. Raine and H. Fanger (1981) J Histo Cyto. 29(4): 577–580. The steps of immunohistochemistry are as follows:

Sections were washed thoroughly in three changes of PBS to remove excess cryoprotectant solution, and sequentially incubated in 5% normal serum, primary antibody, biotinylated-secondary antibody, ABC solution and DAB. Primary antibodies used were α6 integrin (1:100), laminin (1:100), collagen type IV (1:100) and collagen type VII (1:100). All secondary antibodies were applied at dilutions of 1:200. Sections processed without primary antibody were used as negative controls. Following three rinses with sodium cacodylate buffer, sections were kept at 4° C. overnight in half Karnovsky's fixative consisting of 2.5% glutaraldehyde and 1.6% paraformaldehyde in 0.1M sodium cacodylate. Fixed sections were washed thoroughly in three changes with sodium cacodylate buffer, post fixed in 1% osmium tetroxide in 0.1M sodium cacodylate buffer for 2 min., thoroughly rinsed in 0.1M sodium cacodylate buffer, dehydrated in increasing concentrations of ethanol, cleared in propylene oxide and embedded in epoxy resin. Ultrathin sections were counter stained with lead citrate and uranyl acetate and analyzed with a JEOL 1200EX transmission electron microscope.

Results indicated precise immunolocalizations of all subject proteins and acceptable ultrastructural morphology. Alpha 6 integrin immunoreactivity was localized to the outer hemidesmosomal plaques of epidermal basal cells. Immunoreactivity of laminin was localized to the lower aspect of the lamina lucida of the basement membrane zone, with some immunoreactivity in the upper portion of the lamina densa. Immunodetection of collagen type IV was specific to the lamina densa and anchoring plaques. Collagen type VII immunoreactivity was specific to the lower aspect of the lamina densa and to the sublamina densa. In the sublamina densa, collagen type VII immunoreaction products appeared as tubular projections, corresponding to anchoring fibrils. No immunoreaction products of any of the proteins tested were evident in negative control sections.

The present invention provides evidence that the use of free-floating cryostat sections is a valuable procedure for ultrastructural identification of skin basement membrane zone proteins. Using this technique, precise immunolocalizations of all selected proteins are presented, tissue processing from light to electron microscopy is accelerated and correlation of light and electron microscopy in the same tissue section is possible. These desired applications are especially important when results of immunolabeling need to be determined quickly at the level of light and electron microscopy, and will be beneficial in the diagnosis and characterization of targeted antigens associated with vesicating skin lesions.

What is claimed is:

1. A method of viewing a single tissue sample with a light microscope and an electron microscope comprising: placing a free-floating sectioned tissue sample on a floating solution in a well wherein the floating of said tissue sample permits viewing by said light microscope and does not destroy said tissue sample for subsequent electron microscope viewing.

2. The method of claim 1 wherein said tissue sample is about 60 microns thick.

3. The method of claim 1, wherein said tissue sample is a skin basement membrane zone tissue sample.

4. The method of claim 3, wherein said skin basement membrane zone tissue sample contains skin basement membrane zone proteins selected from the group consisting of α6 integrin, pan-laminin, collagen type IV, and collagen type VII.

5. The method of claim 1, further comprising the step of non-specifically staining said tissue sample prior to viewing with a light microscope.

6. The method of claim 5, floating solution comprises a cryoprotectant.

7. The method of claim 6, wherein the cryoprotectant comprises deionized water, sucrose, ethylene glycol, sodium phosphate monobasic, sodium phosphate dibasic, sodium chloride, polyvinylpyrorolidone.

8. The method of claim 7, wherein said cryoprotectant comprises about 500ml deionized water, about 300g sucrose, about 300 ml. ethylene glycol, about 1.59g sodium phosphate monobasic, about 5.47g sodium phosphate dibasic, about 9.0g sodium chloride, about 10g polyvinylpyrorolidone and the final volume adjusted to 1 liter with deionized water.

9. A method of studying the pathogenesis of vesicants on skin that preserves a skin basement membrane zone of said skin and does not compromise zone function comprising:

floating a sectioned tissue sample on a floating solution on a surface, wherein the floating of said tissue sample permits viewing by said light microscope and does not destroy said tissue sample for electron microscope viewing;

subjecting the tissue sample to specific immunohistochemical or cytochemical procedures;

viewing the tissue sample with a light microscope; and viewing the same tissue sample with an electron microscope.

10. A method of studying the pathogenesis of vesicants on skin that preserves a skin basement membrane zone of said skin and does not compromise zone function comprising:

floating an unfixed cryostat skin section sample on a floating solution on a surface, wherein the floating of said skin section sample permits viewing by said light microscope and does not destroy said skin section sample for electron microscope viewing;

subjecting the skin section sample to specific immunohistochemical or cytochemical procedures;

viewing the skin section sample with a light microscope; and viewing the same skin section sample with an electron microscope.

11. The specimen of claim 10, wherein said tissue sample is a skin basement membrane zone tissue sample.

12. The specimen of claim 11 wherein said tissue sample has been subjected to an immunohistochemical procedure or cytochemical procedure prior to viewing.

13. A specimen suitable for viewing by both a light microscope and an electron microscope comprising:

an unfixed cryostat tissue section sample free-floating in a floating solution on a surface; said surface suitable for viewing with said light microscope and permitting subsequent viewing by said electron microscope.

* * * * *